(12) United States Patent
Arias

(10) Patent No.: US 10,386,358 B2
(45) Date of Patent: Aug. 20, 2019

(54) SOBRIETY TEST AUTHENTICATION PROCESS AND DEVICE

(71) Applicant: ALCOSYSTEMS SWEDEN AB, Jaerfaella (SE)

(72) Inventor: Juan Miguel Arias, Stockholm (SE)

(73) Assignee: ALCOSYSTEMS SWEDEN AB, Jaerfaella (SE)

( * ) Notice: Subject to any disclaimer, the term of this patent is extended or adjusted under 35 U.S.C. 154(b) by 21 days.

(21) Appl. No.: 15/525,927

(22) PCT Filed: Nov. 10, 2015

(86) PCT No.: PCT/EP2015/076212
§ 371 (c)(1),
(2) Date: May 10, 2017

(87) PCT Pub. No.: WO2016/075139
PCT Pub. Date: May 19, 2016

(65) Prior Publication Data
US 2017/0307588 A1    Oct. 26, 2017

(30) Foreign Application Priority Data
Nov. 10, 2014 (EP) .................................. 14192472

(51) Int. Cl.
*B60K 28/02* (2006.01)
*G01N 33/497* (2006.01)
(Continued)

(52) U.S. Cl.
CPC ......... *G01N 33/4972* (2013.01); *B60K 28/00* (2013.01); *G06K 9/00288* (2013.01); *B60W 2540/24* (2013.01)

(58) Field of Classification Search
CPC .............. A61K 2300/00; A61K 31/133; A61K 31/137; A61K 31/197; A61K 31/198;
(Continued)

(56) References Cited

U.S. PATENT DOCUMENTS 4,912,458 A * 3/1990 Comeau ............... B60K 28/063
180/272
4,914,038 A * 4/1990 Jewitt .................. B60K 28/063
180/272
(Continued)

FOREIGN PATENT DOCUMENTS

| WO | 0235850 A1 | 5/2002 |
|---|---|---|
| WO | 2012087187 A1 | 6/2012 |
| WO | 2014144834 A1 | 9/2014 |

OTHER PUBLICATIONS

European Patent Office, Extended European Search Report Issued in Application No. 14192472.0, dated Apr. 28, 2015, Germany, 6 pages.
(Continued)

*Primary Examiner* — Daniel Previl
(74) *Attorney, Agent, or Firm* — McCoy Russell LLP

(57) ABSTRACT

Process and device to authenticate a subject undergoing a sobriety test, by testing the blood alcohol content (BAC) of the subject, emitting an indication of the confirmed test, and recording said indication together with a picture of said subject, wherein said indication comprises a representation of a temporary validation code.

19 Claims, 3 Drawing Sheets

(51) Int. Cl.
B60K 28/00 (2006.01)
G06K 9/00 (2006.01)

(58) Field of Classification Search
CPC .............. A61K 31/352; A61K 31/4015; A61K 31/4375; A61K 31/4415; A61K 31/455; A61K 31/51; A61K 31/519; A61K 31/525; A61K 31/714; A61K 31/732; A61K 36/28; A61K 36/73; A61K 36/752; A61K 45/06; A61K 8/19; A61K 8/31; A61K 8/67; A61K 8/673; A61K 9/0095; A61K 9/08; A23V 2002/00; A23V 2200/334; A23V 2250/0616; A23V 2250/0634; A23V 2250/21168; A23V 2250/5072; A23V 2250/7042; A23V 2250/7044; A23V 2250/7046; A23V 2250/705; A23V 2250/7052; A23V 2250/706; A23V 2250/0652; A23V 2250/16; A23V 2250/161; A23V 2250/1614; A23V 2250/7054; A23V 2250/7058; G06Q 40/08; G06Q 40/02; G06Q 50/22; G06Q 50/24; G06Q 10/10; G06Q 40/04; G06Q 50/18; G01N 33/4972; B60W 2540/24; B60W 2050/143; B60W 2550/402; B60W 2040/08; B60W 2040/0836; B60W 40/08; B60W 50/087; G06K 9/00288; G06K 9/00906; B60K 28/00; B60K 28/063; B60K 28/06; B60K 28/066; G06F 19/00; G06F 21/31; A23L 33/15; A23L 33/16; A23L 33/175; A23L 33/21; A61B 2560/0242; A61B 5/0002; A61B 5/18; A61B 2560/0214; A61B 3/14; A61B 5/002; A61B 5/0022; A61B 5/004; A61B 5/01; A61B 5/0205; A61B 5/02055; A61B 5/024; A61B 5/11; A61B 5/1172; A61B 5/145; A61B 5/14507; A61B 5/14542; A61B 5/14551; A61B 5/162; A61B 5/4863; A61B 5/6803; A61B 5/6817; A61B 5/6887; A61B 5/6898; A61B 5/721; A61B 5/7475; H04S 2420/01; H04S 7/00; Y10S 436/90; Y10T 436/204165; A61F 11/10; A61F 2011/085; A61F 2011/145; B60Q 9/00; F02D 17/04; F02D 2041/281; F02D 2200/0406; F02D 2200/60; F02D 2250/26; F02D 2400/11; F02D 41/0097; F02D 41/021; F02N 11/101; F02N 2200/10; F02P 11/04; F02P 5/1502; G06N 7/005; G08C 2201/93; G09B 7/00; G10K 11/002; G10K 2210/1081; H04Q 9/00; H04R 1/1008; H04R 1/1016; H04R 1/1025; H04R 1/1083; H04R 2225/31; H04R 2225/39; H04R 2225/41; H04R 2225/43; H04R 2225/55; H04R 2225/61; H04R 2460/03; H04R 2460/05; H04R 2460/07; H04R 2460/11; H04R 25/00; H04R 25/02; H04R 25/554; H04R 29/004; H04R 5/033
USPC ......... 340/576, 573.1, 574, 575, 665, 691.6, 340/825.29, 5.32, 5.61, 5.8
See application file for complete search history.

(56) References Cited

U.S. PATENT DOCUMENTS

| | | | |
|---|---|---|---|
| 2002/0051577 A1 | 5/2002 | Kinjo | |
| 2004/0083031 A1* | 4/2004 | Okezie | A61B 5/145 701/1 |
| 2011/0292209 A1 | 12/2011 | Morley et al. | |
| 2011/0309932 A1 | 12/2011 | Arringdale et al. | |
| 2013/0021153 A1* | 1/2013 | Keays | G01N 33/4972 340/539.12 |
| 2014/0187993 A1* | 7/2014 | Contestabile | A61B 5/082 600/532 |

OTHER PUBLICATIONS

ISA European Patent Office, International Search Report Issued in Application No. PCT/EP2015/076212, dated Jan. 26, 2016, WIPO, 3 pages.
ISA European Patent Office, Written Opinion of the International Searching Authority Issued in Application No. PCT/EP2015/076212, dated Jan. 26, 2016, WIPO, 5 pages.
IPEA European Patent Office, International Preliminary Report on Patentability Issued in Application No. PCT/EP2015/076212, dated Mar. 22, 2017, WIPO, 12 pages.

* cited by examiner

SOBRIETY TEST AUTHENTICATION PROCESS AND DEVICE

CROSS-REFERENCE TO RELATED APPLICATIONS

The present application is a U.S. National Phase of International Patent Application Serial No. PCT/EP2015/076212, entitled "SOBRIETY TEST AUTHENTICATION PROCESS AND DEVICE," filed on Nov. 10, 2015. International Patent Application Serial No. PCT/EP2015/076212 claims priority to European Patent Application No. 14192472.0, filed on Nov. 10, 2014. The entire contents of each of the above-cited applications are hereby incorporated by reference for all purposes.

TECHNICAL FIELD

The invention concerns a process to authenticate a subject undergoing a sobriety test, where the process comprises the steps of testing the Blood Alcohol Content (BAC) of the subject i.e. a tested person, emitting an indication of a confirmed test (defined as a test, wherein the test result has successfully been captured; whereas a non-confirmed test is defined as an attempted test, wherein test values and other data were not successfully captured by the device, software or due to the person incorrectly using the testing method) when said BAC is within a predefined range (defined as the permitted range of allowed blood alcohol content in the subject's blood; this range will differ according to country, job or other factors; said predefined range may be any continuous or composed range or set of BAC values) and recording said indication of the confirmed test together with a picture of said subject, and a device to authenticate a sobriety test, which device comprises an indicator and a controller connected to said indicator and configured to operate said indicator, wherein said controller is further connected to a sensor arrangement configured to perform a sobriety test and provide a notification of a confirmed test to said controller.

BACKGROUND AND SUMMARY

In this context the term "sobriety test" refers generally to a method for determining and testing the BAC of a subject; in particular it is not limited to determining and/or testing only low or zero BAC values or only ranges below a certain—e.g. legal—BAC limit.

There are several known methods for determining and testing the BAC of a subject. In practice, the BAC is measured in a blood sample of the subject or estimated from a breath alcohol content (BrAC). The latter method allows for quick and easy tests and is therefore wide-spread for different applications ranging from law enforcement to therapy monitoring and professional self-tests. BrAC may be measured using spectroscopy or with fuel cell sensors. The sensor arrangement may in principle comprise any of the known devices capable of determining the BrAC and/or BAC of a subject according to one of the above methods.

WO 2012/087187 A1 discloses a method and an apparatus for measuring BrAC based on a fuel cell sensor. The apparatus is a compact breathalyzer-type device, which displays the measured BrAC or a BAC estimated based on a BrAC measurement. As such, this apparatus is one possible embodiment of a sensor arrangement according to the definition used in the outset.

In case a device of the type disclosed in WO 2012/087187 A1 is used, testing the BAC comprises the steps of determining the BrAC from a breath sample provided by the subject, estimating a BAC from said BrAC, and determining whether the estimated BAC is within a predefined range. Said predefined range may be determined according to legal provisions or to corporate or personal guidelines.

Furthermore it has been suggested to indicate the test condition in a manner recognizable to the subject. In particular, a test device may indicate whether the device is inactive, a measurement or test is in progress, a test is confirmed or a test is non-confirmed. These test conditions may be visually and/or acoustically presented, e.g. on a display of the test device. In this context, the indication of the test condition, in particular of a confirmed test and the test result, can be recorded in order to authenticate the test result as well as the subject carrying out the test. However, it is evident that at least for visual indications, such recording of results and other data can be easily circumvented by subjects trying to avoid an unfavorable test outcome. For instance, a replica of the visual indication (a photo or the like) of an earlier legitimate test can be used to forge the process, while the test itself is carried out on a sample provided by a different, sober person.

A primary object of the present invention is to provide a process to eliminate or at least greatly reduce the risk of illegitimate tests, i.e. where the test result does not represent the condition of a subject being tested, as well as to provide a device for use in such a process.

In order to achieve the objective mentioned above, the present invention provides a process as defined in the outset, wherein said indication comprises a representation of a temporary validation code, meaning that the temporary validation code changes on a case-by-case basis with each individual test or measurement. The temporary validation code is unpredictable by the subject or user, in particular it does not follow any obvious regular pattern. The temporary validation code is generated or received prior to emission of said indication (s. below). Being a code, the temporary validation code is an arrangement of data or information without necessarily conveying any specific meaning or signification in itself other than being usable in connection with the present process. The indication may be any recordable message or signal, preferably one that is also in itself perceivable to a person who may subsequently verify the recorded indication. The representation of the temporary validation code is adapted to the type of indication (i.e. visual, audio-visual, electromagnetic, etc.). In particular the representation does not have to be reversible, i.e. it does not necessarily carry the full information of the temporary validation code. The representation may be a written expression of a part of the temporary validation code corresponding to a certain character encoding; or it may be a sequence of sounds corresponding to an acoustic encoding of (parts of) the temporary validation code.

By recording the indication comprising a representation of the temporary validation code together with a picture of the subject under test, the temporary validation code, confirming the execution of the test and the successful capturing of a test result, and the subject are associated in an unreproducible manner. The emission and recording of (the representation of) the temporary validation code is simultaneous with the recording of the picture, thus creating an association between the temporary validation code (or its recorded representation) and the picture and thereby authenticating the picture. Preferably, both the capturing of the picture and the emission of the temporary validation code are performed immediately subsequent to the test, i.e. as soon as the test is finished and the test result is obtained. Therefore the picture shows the subject at the moment of the test result being captured or transmitted (or shortly thereafter; e.g. within a maximum latency of one second). The picture preferably shows the face of the subject while carrying out the test. In order to forge an authentic picture, a user would have to guess a valid temporary validation code in advance and provide a forged indication while doing and recording the test. It is therefore much harder, if at all possible, to forge the process.

The temporary validation code may also be used with other data captured during the confirmed test, such data may include but not limited to time-stamp, geo-location, latitude, atmospheric pressure, weather conditions.

Correspondingly, in order to achieve the objective mentioned above and with similar advantages, the present invention further provides a device as defined in the outset, wherein said controller is configured to operate said indicator to emit a representation of a temporary validation code when a notification of a confirmed test is provided by said sensor arrangement. The controller may comprise one or several components. The controller may be configured to receive a test result transmitted by said sensor arrangement or the controller may be part of the sensor arrangement, having access to the test result. The controller is further configured to generate or receive a temporary validation code. The indicator may be any device or arrangement capable of showing or otherwise communicating a representation of the temporary validation code as defined above. For instance it may be a display or speaker; it may also be a means for data transmission, allowing for electronic recording of (the representation of) the temporary validation code.

In a particularly advantageous embodiment, the sensor arrangement is integral with said device; more specifically, the sensor arrangement, the controller and the indicator may be integrated in one common unit or housing, thus providing a compact device for performing and authenticating sobriety tests.

Preferably the representation of the temporary validation code is a visual representation of the temporary validation code. Thus a visual representation of the temporary validation code is emitted as an indication of the confirmed test. Such temporary validation code may be visible to the test subject or may only be visible to those who have administrative rights to manage test results at the backend.

In this case the recorded picture of the subject may include an image of said visual representation according to the temporary validation code. A simple photograph, wherein the subject doing the test and the indication are in the same view field of a camera, suffices to authenticate the picture and the subject pictured thereon. The picture can be made with any smart computer device, such as a mobile phone, a car computer, an airplane computer or a factory access unit, comprising or being connected to a digital camera and the test may be recorded using a specialized app, preferably giving immediate feedback on the successful authentication. The visual representation of the temporary validation code can be a visual signal or a displayed message.

Correspondingly the indicator of the present device is preferably a visual indicator. In particular the indicator can be a display or light source, e.g. a light-emitting diode (LED). Besides the above-mentioned advantages of visual indications in connection with the authentication of the picture, such indicators are also relatively inexpensive and small and at the same time easy to handle and reliable compared to acoustic or electronic indicators.

Advantageously said visual representation is a color, wherein said indication is a flash of correspondingly colored light. The color may be selected from a set of predefined colors, the selection being based on the temporary validation code. Use of a color (e.g. red, green, blue, etc.) simplifies detection and verification of the representation within the picture. Also, emission of a flash of colored light, wherein the color of the flash light represents the temporary validation code, can be accomplished by a simple and inexpensive multicolor LED.

In order to associate the temporary validation code (i.e. the recorded representation thereof, which is comprised in the recorded indication) not only with a test instance but with a test result, the preset process may comprise the steps of emitting a representation of a test result of said test at the same time as said indication of the confirmed test, and recording said representation of the test result together with said indication and picture. Such an essentially simultaneous emission and recording of the test result and the temporary validation code creates a unique link between these two values. By this link or association, not only the sobriety test as such, but—more specifically—the test result can be authenticated.

If said indication comprises said representation of the test result, the emission and recording steps can be greatly simplified, because the same medium can be used for indication of the confirmed test as well as the test result. For instance, the emission of the representation of the temporary validation code can be preceded or succeeded by a similar indication of the test result. Or the temporary validation code itself contains an indication of the test result.

In another alternative, the process is characterized further by emitting said indication only when said BAC is within a predefined range, wherein said indication is an indication of a confirmed test with a test result signaling a sober subject or a subject at least having a BAC within said predefined range (i.e. an indication of a positive test result). In this instance, the emission of a temporary validation code already in itself, i.e. by its mere presence, expresses the finding of a positive test result corresponding to a sober subject. Because the test is a sobriety test, the term "positive" here refers to the sobriety of the subject. Since sobriety is defined as a BAC within the predefined range, whether or not the process and device described here (and with the above) are used to determine if the subject has a BAC between zero and a certain limit (or above that limit) is only and exclusively a question of the employed predefined range. On the other hand, if the subject is not sober, the sobriety test yields a negative test result.

In order to obtain an unpredictable temporary validation code the present process may comprise the step of generating said temporary validation code at random (e.g. using a random number generator) before emitting said indication and associating the generated temporary validation code with a test result. The test result can be recorded as such or through its representation in the recorded indication, in which latter case the generated temporary validation code would be associated with the recorded indication. In any case, the recorded representation of the temporary validation code is directly or indirectly (via the test result) associated with the generated temporary validation code and the picture of the subject. The authenticity of the picture can therefore be verified by comparing the recorded representation (recorded at the same time as the picture, as described above) with the associated validation code, e.g. by reproducing a similar representation from the associated validation code during verification. For instance when using a color representation, a color code may be associated with the picture and a corresponding color name (different representation) displayed next to the picture for verification of a recorded flash of colored light. Similar procedures may be applied e.g. to acoustic representations by comparing a recorded sound with a sound regenerated from an associated validation code.

In order to avoid the necessity of storing and transmitting the temporary validation code along with the picture and test result, which may be vulnerable to manipulation, the present process may instead comprise the step of deriving said temporary validation code from a time-stamp associated with a test result. The generation of the temporary validation code may follow a predefined algorithm, e.g. an encryption or the like, which is reproducible for verification of the validation code. During validation of a given picture and associated test result, the validation code may be first reproduced from a time-stamp of that picture and then the reproduced validation code is compared with the recorded representation. Naturally, the algorithm for deriving the validation code from the time stamp must remain secret. This may be achieved by implementing the algorithm in tamper-proof hardware or by similar measures.

For use-cases where professional self-tests are required, it is particularly useful to allow for central storage and verification of performed tests. In the present process this can be achieved by communicating with a remote database and transmitting a test result, the recorded indication (thus including the representation of said temporary validation code) and the recorded picture of said subject, as well as information associated with said test result where applicable (e.g. time-stamp and/or validation code), to said remote database. The test results provided by employees can thus be conveniently accessed and verified via said remote database. This is particularly useful where verification requires human interaction (e.g. for confirming the identity of a subject with the recorded picture and for comparing representations of validation codes), which can then be performed through a centralized procedure.

Additionally or alternatively the present process may comprise locally storing a test result, the recorded indication and the recorded picture of said subject, as well as information associated with said test result where applicable. In particular the protocol comprising the test results and any associated recorded information (at least a picture and a recording of the indication for each test result) can be stored locally in an encrypted format and optionally transmitted at a later time. This allows the application of the process even in offline applications, e.g. at workplaces underground.

The present device therefore preferably comprises a data transmission unit connected to said controller and configured to transmit a test result together with information allowing verification of said representation of the temporary validation code. For instance the temporary validation code may be transmitted as such or, when the code can be derived from a time-stamp, that time-stamp is transmitted. The data transmission unit may be a wireless transmission unit, e.g. a Bluetooth unit, for connection with a mobile phone or other digital devices of the subject under test.

To further improve the security of the test authentication or at least to provide information related to the circumstances of the performed tests, which may be useful to apply different guidelines to each test result according to the circumstances, the present process may comprise the step of associating additional test-related information with the test result, wherein said information comprises a blood alcohol content determined during the test, an assumed identity of the tested subject (i.e. the identity of a requested test subject), a geographic location of the test, a moment of test (i.e. date and time of the test), a latitude of the test (e.g. for on-flight tests), a hardware address of a test device (e.g. a MAC address of the test device) or a phone number of a communication device connected with said test device (e.g. a mobile phone or any other digital device used for establishing a connection between the test device and a remote database). The additional information may be used to confirm the validity of a recorded test, e.g. by comparing an associated hardware address with the hardware address of a personal test device of the subject and/or comparing an associated phone number with the personal phone number of the subject.

Specific authentication of test-related information can be achieved by assigning the temporary validation code to the additional test-related information. Said assigning may be achieved by associating the corresponding pieces of data, e.g. in a record or database, or by wrapping up or packaging the validation code together with the additional test-related information for storage or transmission. For example the validation code can be based on said additional information or derived therefrom or said additional information may be at least partly embedded in the temporary validation code.

BRIEF DESCRIPTION OF THE FIGURES

The invention will be defined in more detail below by means of a preferred exemplary embodiment, to which it is not to be limited to, however, and with reference to the drawings. In detail.

DETAILED DESCRIPTION

Figure 1:
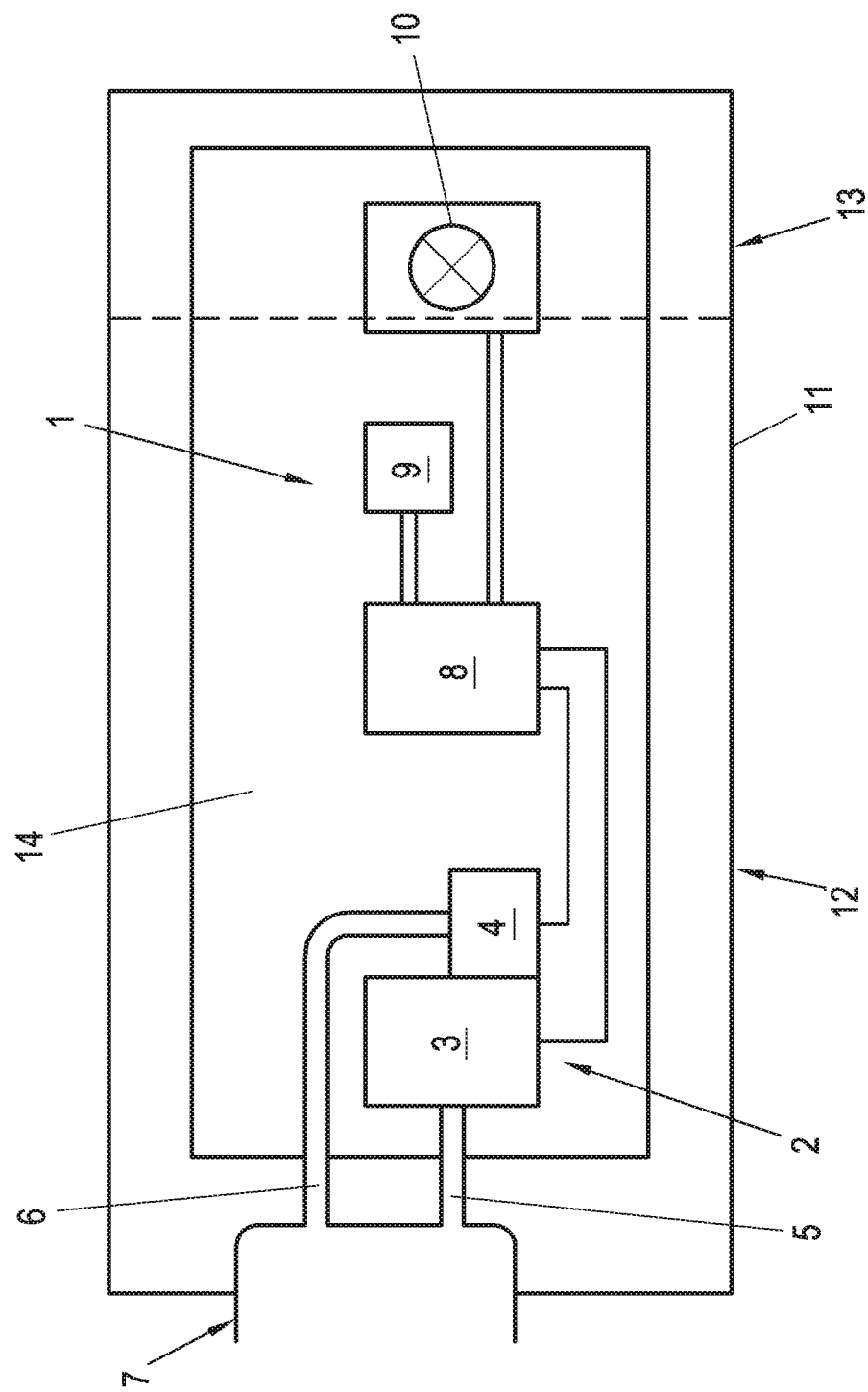
FIG. 1 shows a schematic block diagram of a test device according to the invention.

FIG. 1 shows a device 1 comprising a sensor arrangement 2 for measuring a BrAC and performing a sobriety test. The sensor arrangement 2 comprises a fuel cell 3 and a pressure sensor 4, both connected via corresponding ducts 5, 6 to a mouth piece 7 of the device 1. The device 1 further comprises a controller 8 connected to each of the sensors 3, 4 of the sensor arrangement 2. The controller 8 is configured to operate the sensors 3, 4 in order to perform a measurement of a relative alcohol concentration and pressure of a breath sample provided by a subject blowing into the mouth piece 7, thus forming part of the sensor arrangement 2. The controller 8 is configured to compute a BrAC corresponding to the measured relative alcohol concentration and pressure and estimate a BAC of the subject based on the computed BrAC. The controller 8 comprises an internal memory storing a predefined range of acceptable BAC levels. After estimating the BAC, the controller 8 compares the estimated BAC with the limits of the predefined range and determines a test result based on these comparisons. If the estimated BAC is within the predefined range, a positive test result is obtained (i.e. the subject is sober), otherwise a negative test result is obtained (i.e. the subject is not sober). The controller 8 is further configured to provide and process an internal notification of a confirmed test when the test has been carried out successfully and the test result obtained. The device 1 further comprises a data transmission unit 9 connected to the controller 8. The data transmission unit 9 is a Bluetooth unit adapted for communication with nearby Bluetooth transmitters and configured to transmit the measured BrAC, the estimated BAC and/or the obtained test result. Finally the device 1 comprises an indicator 10, which is a LED. The indicator 10 is connected to the controller 8 such that the activity and color of the LED is controllable by the controller 8. The controller is configured to operate said indicator 10 to emit a representation of a temporary validation code upon the notification of a confirmed test. The sensor arrangement 2, the controller 8, the transmission unit 9 and the indicator 10 are contained in a common housing 11 of the device 1. The housing 11 has an opaque section 12 and a partially transparent section 13 in proximity to the indicator 10, which transparent section 13 allows for light transmission from the indicator 10 inside the housing 11 to the outside of the housing 11. The indicator 10, the controller 8, the data transmission unit 9 and the sensor arrangement 2 are mounted on a common circuit board 14, which allows for easy interconnection between the respective elements. The device 1 further comprises a battery (not shown for simplicity) for powering at least the controller 8, the data transmission unit 9 and the sensor arrangement 2.

Figure 2:
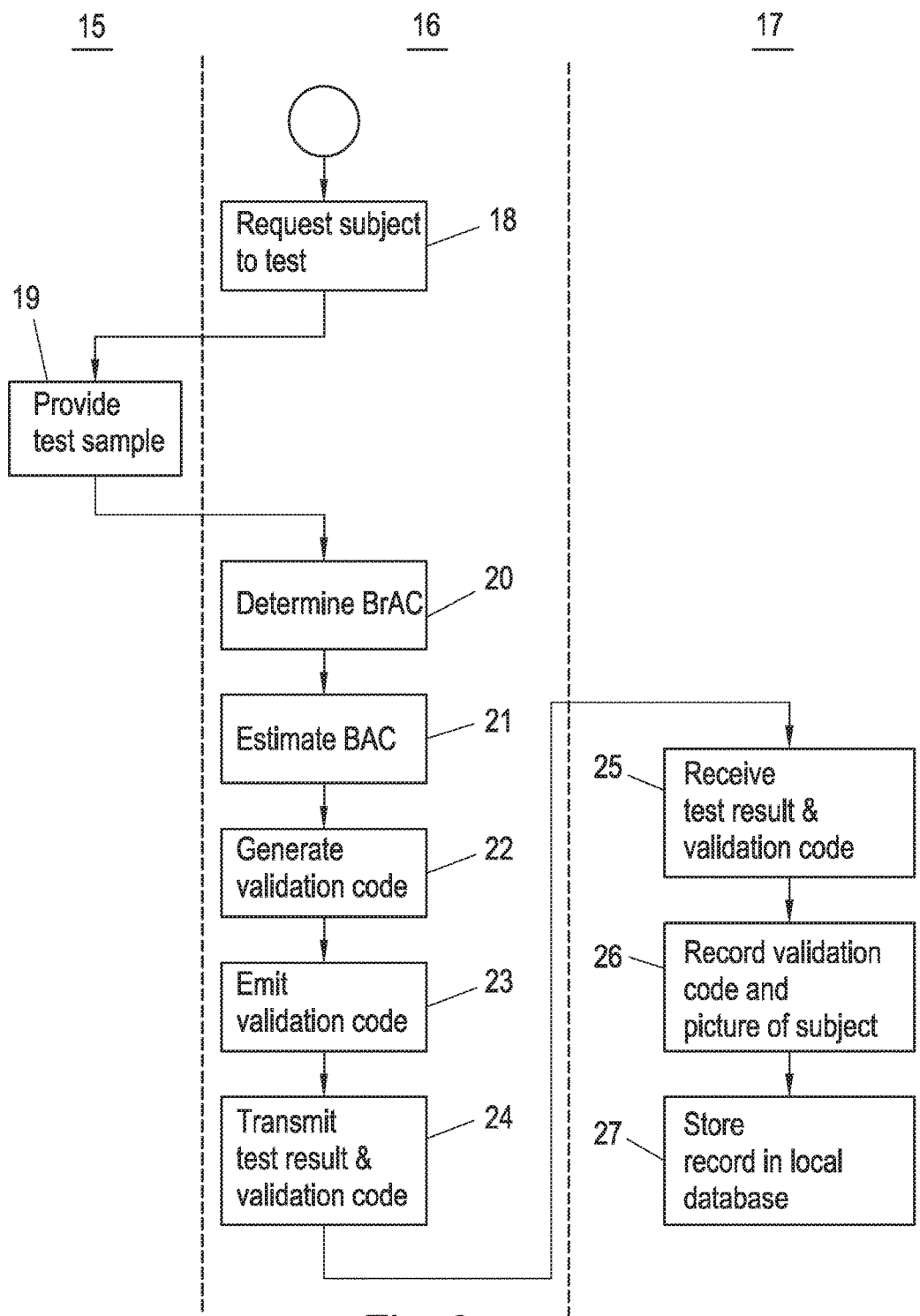
FIG. 2 shows a schematic flow chart of a test procedure according to the invention.

The flow process chart in FIG. 2 illustrates the steps of a typical sobriety test using the device 1 shown in FIG. 1. In order to appropriately reflect the role of the device 1, the chart in FIG. 2 is partitioned in "swim lanes" 15, 16, 17, wherein the central lane 16 comprises the steps performed by the device 1, the left lane 15 comprises the steps carried out by a subject performing the test and the right lane 17 comprises the steps performed by a third-party digital device (e.g. a smart computer device; see below), which is connected to the device 1. The test is initialized by requesting a subject to test (box 18). This is performed by visual notification on the test device 1, specifically by a repeatedly flashing blue indicator 10. Following the request 18, the subject activates a personal mobile phone connected with the device 1 via the data transmission unit 9 and points a camera of the mobile phone to his face as he provides a test sample (box 19); otherwise a refusal to test is recorded and reported. The test sample is provided by blowing into the mouth piece 7, providing a breath sample. While providing the test sample, the device 1 indicates a "test in progress" condition by a continuous orange light emitted by the indicator 10. As soon as a sufficient sample has been taken, the BrAC of that sample is determined (box 20) and a BAC is estimated based on the determined BrAC (box 21). During this phase the "test in progress" condition remains and the subject is required to keep blowing to ensure that the device 1 is not removed from the mouth of the subject. This can be verified by monitoring the breath pressure. A random temporary validation code is generated (box 22) and a color out of a predefined set of colors is selected based on the generated validation code as its representation. When the test is finished and confirmed and the estimated BAC available, the indicator 10 emits the representation of the temporary validation code by glowing in the selected color (box 23). At the same time the test result which corresponds to the result of a comparison of the estimated BAC with a predefined range of acceptable BAC, is transmitted (box 24) to the mobile phone together with the generated validation code via the data transmission unit 9. At the moment of reception (box 25) of the test result and the validation code from the device 1, the mobile phone takes a picture of the user still blowing into the mouth piece 7 of the device 1, thus recording (box 26) the displayed representation of the validation code (the color of the indicator 10) and the face of the subject (thus allowing its identification). Finally the mobile phone locally stores (box 27) a protocol record including the test result (whether within the predefined range, i.e. a sober subject, or falling outside the range, i.e. not a sober subject), the estimated BAC, the validation code, the representation of the validation code (the name of the selected color) and the associated picture showing the subject and comprising the representation of the validation code, allowing for later authentication of the test. The local protocol storage is protected against manipulation, e.g. by using suitable encryption or digital signatures.

Figure 3:
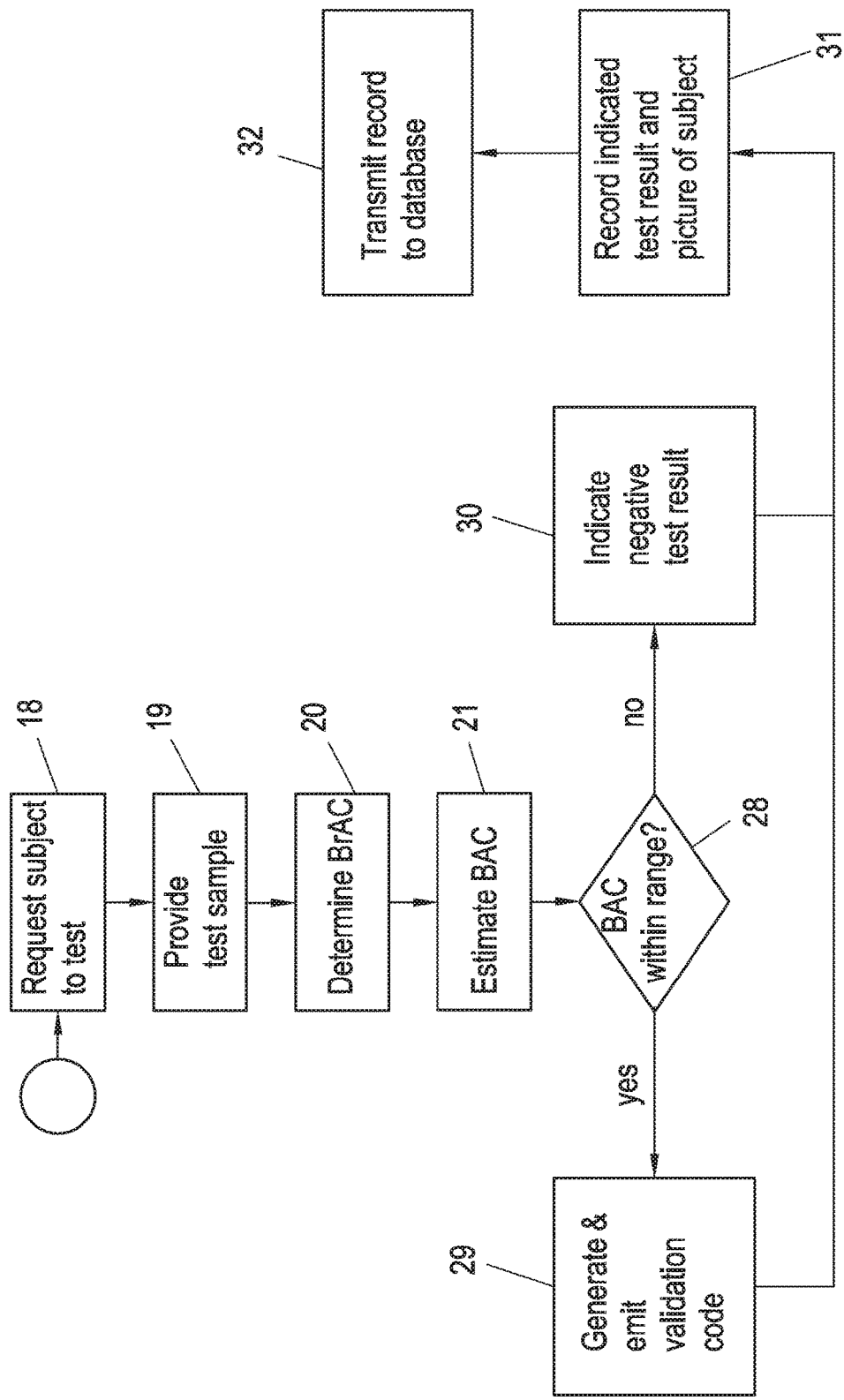
FIG. 3 shows a schematic flow chart of an alternative test procedure according to the invention.

The flow process chart in FIG. 3 illustrates the steps of an alternative sobriety test procedure usable with the device 1 shown in FIG. 1. The first steps of the test are similar to the process shown in FIG. 2: the test is initialized by requesting (box 18) a subject to test. Following the request 18, the subject provides (box 19) a test sample; otherwise a refusal to test is recorded and reported. As soon as a sufficient sample has been taken, the BrAC of that sample is determined (box 20) and a BAC is estimated (box 21) from the determined BrAC. Differing from the process shown in FIG. 2, the estimated BAC is then compared (box 28) with the predefined range of acceptable BAC and the test confirmed. Only if the estimated BAC is within the range, a temporary validation code is generated (box 29) based on a time-stamp provided by an internal clock of the controller 8, the temporary validation code is mapped to a color code and the color code is transmitted to the indicator 10, which in turn emits a flash of light according to the received color code. On the other hand, if the estimated BAC is out of the predefined range, a negative test result is indicated (box 30) by a different flash of light (of a particular predefined color e.g. white) emitted by the indicator 10. At the same time as the respective colored flash (i.e. random color or white) is emitted by the indicator 10, the device 1 sends a command to the mobile phone via the data transmission unit 9 to take a picture at this moment and comprising a time-stamp for the picture. Upon receiving said command, the phone records (box 31) the test result indicated by the flashing indicator 10 by capturing and saving a picture of the subject and the device 1. The captured picture shows the face of the subject (thus allowing its identification) while blowing into the mouth piece 7 of the device 1 with the indicator 10 of the device 1 indicating the test outcome by emitting either a colored flash according to a temporary validation code, which in turn is based on the time-stamp of the picture, to indicate a confirmed test and a test result within the predefined range (positive test result), or a particular predefined color flash to indicate a test result falling outside the predefined range (negative test result). Subsequently the mobile phone transmits (box 32) a protocol record comprising the recorded picture showing the subject, the indication and including the time-stamp of the test and optionally the test result (within or outside the predefined range), the BrAC and/or BAC to a central database via a WiFi or cellular data connection of the mobile phone.

While the processes in FIGS. 2 and 3 are described in connection with the use of a mobile phone together with the device 1 of FIG. 1, the mobile phone may be replaced by any digital device, such as a car computer, a laptop, an airplane computer or a factory access unit, within the scope of the present invention. Especially in connection with different applications, ranging from alcolock-systems for cars or planes (based on embedded systems) to protection of personnel in hazardous workplaces, which require exceptional mental and physical conditions, (where fixed test installations may be provided) to personal supervision (e.g. of adolescent children going out) (where mobile appliances as the one described in detail above will be preferred), different types and form factors of the device itself as well as communicating devices will be envisaged by the skilled person within the scope of the present invention.

The invention claimed is:

1. A process to authenticate a subject undergoing a sobriety test, comprising the following steps:
   testing a blood alcohol content (BAC) of the subject, generating a temporary validation code, wherein the generated temporary validation code changes on a case by case basis with each individual sobriety test and is unpredictable to the subject,
   emitting a visual representation of the temporary validation code as an indication of a confirmed sobriety test, and
   recording a photograph of the subject and the emitted visual representation of the temporary validation code with a camera,
   wherein the subject doing the sobriety test and the emitted visual representation are in a same view field of the camera.

2. The process according to claim 1, wherein said visual representation is a color, wherein said indication is a flash of a correspondingly colored light, and further comprising selecting the color based on the temporary validation code.

3. The process according to claim 2, wherein emitting said indication of the confirmed sobriety test occurs only when said BAC is within a predefined range, and wherein said indication of the confirmed sobriety test is an indication of a positive test result.

4. The process according to claim 1, further comprising emitting a representation of a test result of said sobriety test at the same time as said indication of the confirmed sobriety test, and recording said representation of the test result together with said photograph.

5. The process according to claim 4, wherein said indication of the confirmed sobriety test comprises said representation of the test result.

6. The process according to claim 4, further comprising associating additional test-related information with the test result, wherein said information comprises the BAC determined during the sobriety test, an assumed identity of the subject, a geographic location of the sobriety test, a moment of test, a latitude of the sobriety test, a hardware address of a test device and/or a phone number of a communication device connected with said test device.

7. The process according to claim 6, wherein associating the additional test-related information with the test result is by assigning the temporary validation code to the additional test-related information.

8. The process according to claim 1, wherein said temporary validation code is generated at random before emitting said indication of the confirmed sobriety test, wherein the process further comprises associating the generated temporary validation code with a test result.

9. The process according to claim 1, further comprising deriving said temporary validation code from a time-stamp associated with a test result.

10. The process according to claim 1, further comprising communicating with a remote database and transmitting a test result, the recorded photograph, as well as information associated with said test result where applicable, to said remote database.

11. The process according to claim 1, further comprising locally storing a test result, the recorded photograph, as well as information associated with said test result where applicable.

12. A device to authenticate a sobriety test, comprising a visual indicator and a controller connected to said visual indicator and configured to operate said visual indicator, wherein said controller is further connected to a sensor arrangement configured to perform the sobriety test and provide a notification of a confirmed sobriety test to said controller, wherein said controller is configured to generate a temporary validation code, wherein the generated temporary validation code changes on a case by case basis with each individual sobriety test such that the temporary validation code is unpredictable to a subject of the sobriety test and is at least partially independent of an outcome of the sobriety test, and wherein the controller is configured to operate said visual indicator to emit a visual representation of the generated temporary validation code when the notification of the confirmed sobriety test is provided by said sensor arrangement.

13. The device according to claim 12, wherein said sensor arrangement is integral with the device.

14. The device according to claim 12, further comprising a data transmission unit connected with said controller and configured to transmit a test result together with information allowing verification of said visual representation of the generated temporary validation code.

15. The device according to claim 14, wherein the controller is configured to operate said visual indicator to emit light having a color selected based on the temporary validation code, and wherein the information allowing verification of said visual representation of the generated temporary validation code includes a name of the selected color.

16. The device according to claim 12, further comprising, wherein the controller is configured to generate the temporary validation code prior to emission of the visual representation.

17. A process to authenticate a subject undergoing a sobriety test, comprising the following steps:
   testing a blood alcohol content (BAC) of the subject, emitting an indication of a confirmed sobriety test, wherein said indication comprises a visual representation of a temporary validation code, whereas the temporary validation code changes on a case by case basis with each individual sobriety test and is unpredictable to the subject, and
   recording with a camera a photograph of said indication and said subject, wherein the subject doing the sobriety test and the indication are in a same view field of the camera.

18. The process according to claim 17, further comprising:
   randomly generating the temporary validation code before emitting said indication, and
   associating the generated temporary validation code with a sobriety test result.

19. The process according to claim 17, further comprising:
   deriving the temporary validation code from a time-stamp associated with a sobriety test result before emitting said indication.

* * * * *